(12) United States Patent
Coeurveille

(10) Patent No.: US 6,377,342 B1
(45) Date of Patent: Apr. 23, 2002

(54) LUMINOMETER, PARTICULARLY FOR MEDICAL ASSAYS

(75) Inventor: Michel Coeurveille, Saint Jean d'Illac (FR)

(73) Assignee: Societe Francaise de Recherches et d'Investissements (SFRI), Saint Jean d'Illac (FR)

( * ) Notice: Subject to any disclaimer, the term of this patent is extended or adjusted under 35 U.S.C. 154(b) by 0 days.

(21) Appl. No.: 09/029,632

(22) PCT Filed: Sep. 3, 1996

(86) PCT No.: PCT/FR96/01344

§ 371 Date: Mar. 24, 1998

§ 102(e) Date: Mar. 24, 1998

(87) PCT Pub. No.: WO97/09610

PCT Pub. Date: Mar. 13, 1997

(30) Foreign Application Priority Data

Sep. 4, 1995 (FR) .............................................. 95 10503

(51) Int. Cl.⁷ .......................... G01N 21/01; G01N 21/76
(52) U.S. Cl. ....................... 356/244; 356/440; 356/246; 422/52; 422/65; 422/82.05
(58) Field of Search .................................. 356/244, 246, 356/440; 422/52, 65, 82.05, 82.08; 436/172, 47

(56) References Cited

U.S. PATENT DOCUMENTS

| 5,063,024 A | * | 11/1991 | Partanen et al. | ............. | 356/246 |
| 5,082,628 A | * | 1/1992 | Andreotti et al. | ............. | 356/434 |
| 5,290,513 A | * | 3/1994 | Berthold et al. | ............. | 356/246 |
| 5,401,465 A | * | 3/1995 | Smethers et al. | ............. | 356/440 |

FOREIGN PATENT DOCUMENTS

| EP | 0 194 102 | 9/1986 |
| EP | 0 286 119 | 10/1988 |
| EP | 0 523 521 | 1/1993 |
| WO | WO 93/22657 | 11/1993 |
| WO | WO 95/11441 | 4/1995 |

* cited by examiner

*Primary Examiner*—Hoa Q. Pham
(74) *Attorney, Agent, or Firm*—Young & Thompson

(57) ABSTRACT

A luminometer includes a chassis protected by a cover whose interior is accessible past a closure flap, a detector for measuring photons with a measuring window, a platform for supporting specimen plates, fixed or able to be displaced along a system of orthogonal axes X, Y and Z, along at least one of the axes of the plane X or Y, and an electronic module for amplification and digitizing of data and an electronic module for processing these data, with the measuring detector being movable and the luminometer having elements for displacement in translation of this detector along the Z axis.

12 Claims, 8 Drawing Sheets

LUMINOMETER, PARTICULARLY FOR MEDICAL ASSAYS

BACKGROUND OF THE INVENTION

The present invention concerns a luminometer adapted for rapid assay of a large number of specimens of small volume, particularly in the field of medical assays.

The luminometer of the present invention is intend to be integrated into the movable head of an assay apparatus with multiple functions.

DESCRIPTION OF THE RELATED ART

There are known luminometers permitting measurement of the light emitted during chemical reactions in specimens contained in plates, particularly so-called microtitration.

Thus there is described in U.S. Pat. No. 5,290,513 a luminometer comprising:

a base with a cover, a first platform movable along the X axis, provided to receive a microtitration plate in the wells of which are distributed specimens of the product to be assayed.

a second platform movable along the Y axis, supporting a detector comprising a body, a head disposed at the end of an arm connected to said body, the body being articulated about an axis of an arm such as a record player arm with resilient return means adapted to press the head downwardly, in the Z direction.

This luminometer is also provided with a fixed mask for guidance and occlusion. This mask comprises a central groove oriented along the Y axis, so as to guide the head which is applied by resilient return means against the mask and more particularly in the groove, when the head is displaced along the Y axis.

A sealing sleeve completes the connection between the head and the groove to avoid penetration of parasitic photons.

The operation of this apparatus is as follows:

emplacement of a plate of specimens, the arm being raised and hence the head being retracted, lowering of the arm and the head into the groove, displacement of the plates stepwise along the X axis to assay all the specimens of one row, displacement of the head along the Y axis by one step to assay all the specimens of the following row, and so on.

Such a system permits applying the head with a given pressure against the mask, thereby ensuring good sealing, but this problem is actually transferred to the interface between the plate and the mask.

Also, this reference proposes pressing the microtitration plate against the lower surface of the mask by interposing a bit of foam between the microtitration plate and the platform which supports it, which rests at random over such a large surface without taking account of the fact that the return power of a foam is only difficultly controllable over all its surface.

It will be noted moreover that the detector is spaced from the measuring site by a distance equal to the length of the arm, which distance can only with difficulty be reduced because it is necessary to be able to have access to all of the surface of the microtitration plate, and also there is provided the interposition of a fiber optic connection.

The losses and errors arising from this connection are not negligible.

Such an apparatus solves some problems but gives rise to others. On the other hand, there results a certain compactness, which is very advantageous in assay laboratories and this advantage must be preserved and even improved for apparatus to come.

Another patent application, EP-A-181 060, discloses a measuring head permitting effecting sealing with the specimen support plate. In this embodiment, the detector is also distant from the measuring head and above all the specimen support plate is specific, according to a certain standardization.

Finally, it can be noted that there is not suggested, in this application, means for displacing the head along coordinates relative to the specimen support plate.

SUMMARY OF THE INVENTION

The object of the present invention is to overcome the drawbacks of the luminometers of the prior art by arranging a measuring detector directly on a support displaceable at least along Z such that it comes to bear directly on the reaction recesses as wells of a microtitration plate or on any other small volume container. This type of detector, developed and used in other applications particularly for transmission by optical fibers, is resistant to vibrations, to accelerations and to microshocks arising from high speed displacements. Its sensitivity is not necessarily as great as that of the detectors of the reaction photomultiplier type, but it is compensated in all cases by the proximity of the detector relative to the source of emission, by the fact that the connection is the transmission of an electric signal and not a luminous signal because the signal is transformed in the detector itself, and also by the fact that, as in the prior art, there are no disturbances engendered by photons that are external or simply emitted by the adjacent specimens, so called cross-contamination.

The invention also has for its object the integration of such luminometer in the working head of a particular apparatus ensuring also the measurement of several parameters having been the object of a patent application in the name of the present applicant and bearing the number EP-A-92/450 011. This apparatus, which is of very high performance, has a very high speed displacement head leading to accelerations of the order of 2 g.

To this end, the luminometer according to the invention comprises a chassis protected by a cover whose interior is accessible through a closure flap, a photon measuring detector with a measuring window, a support platform for specimen plates, fixed or with means to displace said plate along a system of orthogonal axes X, Y and Z, oriented preferably but not necessarily with the Z axis vertical, according to at least one of the axes of the plane X or Y, an electronic module for amplifying and digitizing data and an electronic module for processing these data, and this luminometer is characterized in that the measuring detector is movable and in that it comprises means for displacement in translation of this detector at least along the Z axis.

According to a preferred embodiment, the chassis is provided with displacement means in translation only, along one of the axes of the plane, the Y axis, and the detector and the means for displacement along the Z axis are carried by means for displacement in translation along the other of the axes of the planes, the X axis.

More particularly, the Z displacement means comprise a carriage mounted slidably on a rail oriented along the Z axis and a motor with an integrated encoder secured to a casing, driving a cam in rotation provided to ensure said translatory displacement, this casing being carried by a carriage mounted slidably on a rail, supported by a beam supported at one of its ends, oriented along the X axis, said carriage being driven by an assembly of a belt stretched between a roller and a pulley of a motor with an integrated encoder.

There is also provided an abutment at one of the ends of the movement in the X direction, provided with an end of path detector permitting initiating the displacements, with a black well permitting parking the detector sheltered from parasitic disturbances and with a calibrating lamp disposed in said black well permitting calibrating the detector as needed.

According to a particular embodiment, the electronic module for amplifying and digitizing the data is carried by the means for displacement along the X axis and is disposed in immediate adjacency to the detector.

The detector comprises a photomultiplier and an electronic module for the acquisition of integrated measurements, the assembly being protected by shielding.

According to an improvement of the invention, sealing means and means for compensating for planarity in line with the measuring window are added.

The invention also relates to a measuring device comprising at least one support for a microtitration plate, a movable head, provided with means for measuring the difference physico-chemical parameters, means for displacement in translation of said head along the X and Y axes, this device comprising a luminometer integrated in the head provided with the only means for displacement in translation along the Z axis.

The displacement cam of the preceding embodiment is replaced by a screw and nut assembly.

BRIEF DESCRIPTION OF THE DRAWINGS

The invention is described hereafter with respect to the accompanying drawings, on which are represented an embodiment of an autonomous and automatic luminometer and a measuring head according to the teaching of the European patent mentioned above, in which is integrated the detector portion, the means for displacement along the Z axis of such a luminometer, as well as the electronics for data acquisition, the different figures showing.

DESCRIPTION OF THE PREFERRED EMBODIMENT

Figure 1:
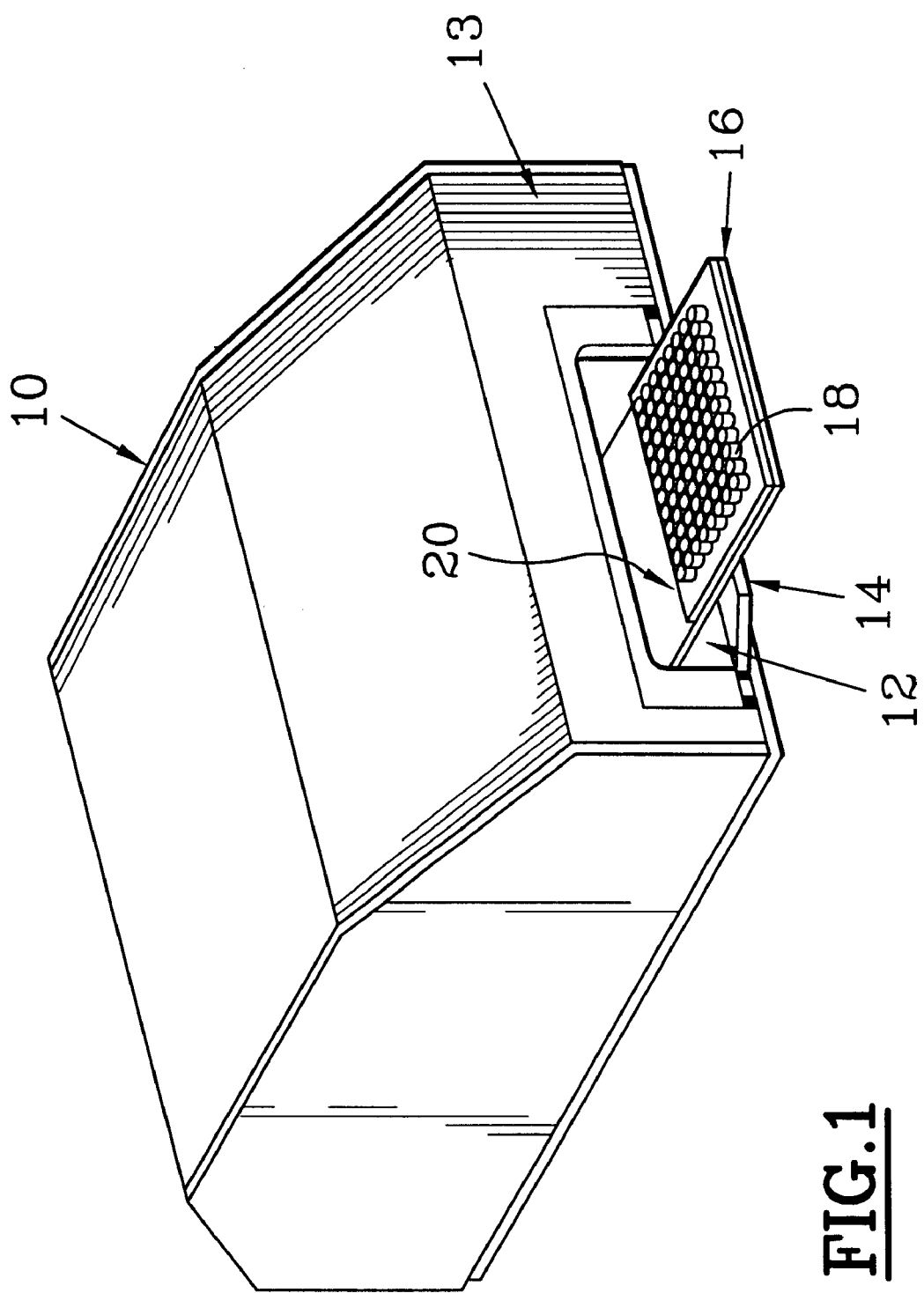
FIG. 1, an overall view of the automatic and autonomous luminometer according to the invention, with its cover, FIG. 2, a view from above of the luminometer after retraction of the cover, FIG. 3, a side elevational view of the luminometer of FIG. 2, FIG. 4A, a detail view, in cross section, perpendicular to the X axis, of the Z displacement means of the detector, FIG. 4B, a side elevational view in the direction of arrow F of FIG. 2, of the Z displacement means, FIG. 5, a detail view of the detector and of its shock absorbing system, FIG. 6, an overall view of the measuring apparatus which is the object of the application EP-A-92/450 011, called ALPHA 4 in commerce, FIG. 7, a schematic view of the interior of the measuring apparatus of FIG. 6, FIG. 8, a view of the measuring head with its protective casing, FIG. 9, a view of the luminometer integrated into the measuring head.

In FIG. 1, there is shown in perspective a luminometer according to the invention, as seen by the user. This luminometer comprises a cover 10 over three of its surfaces and an opening 12 on the front surface 13, closed by a swinging flap 14. In this figure, there is also shown a microtitration plate 16 comprising microwells 18, resting on a movable platform 20.

To give the overall picture, the luminometer has a size in length and width, each substantially equal to twice the dimensions respectively in length and width, of a standard assay plate, which shows the compactness of such an apparatus, as will be confirmed by the details given hereafter.

Figure 2:
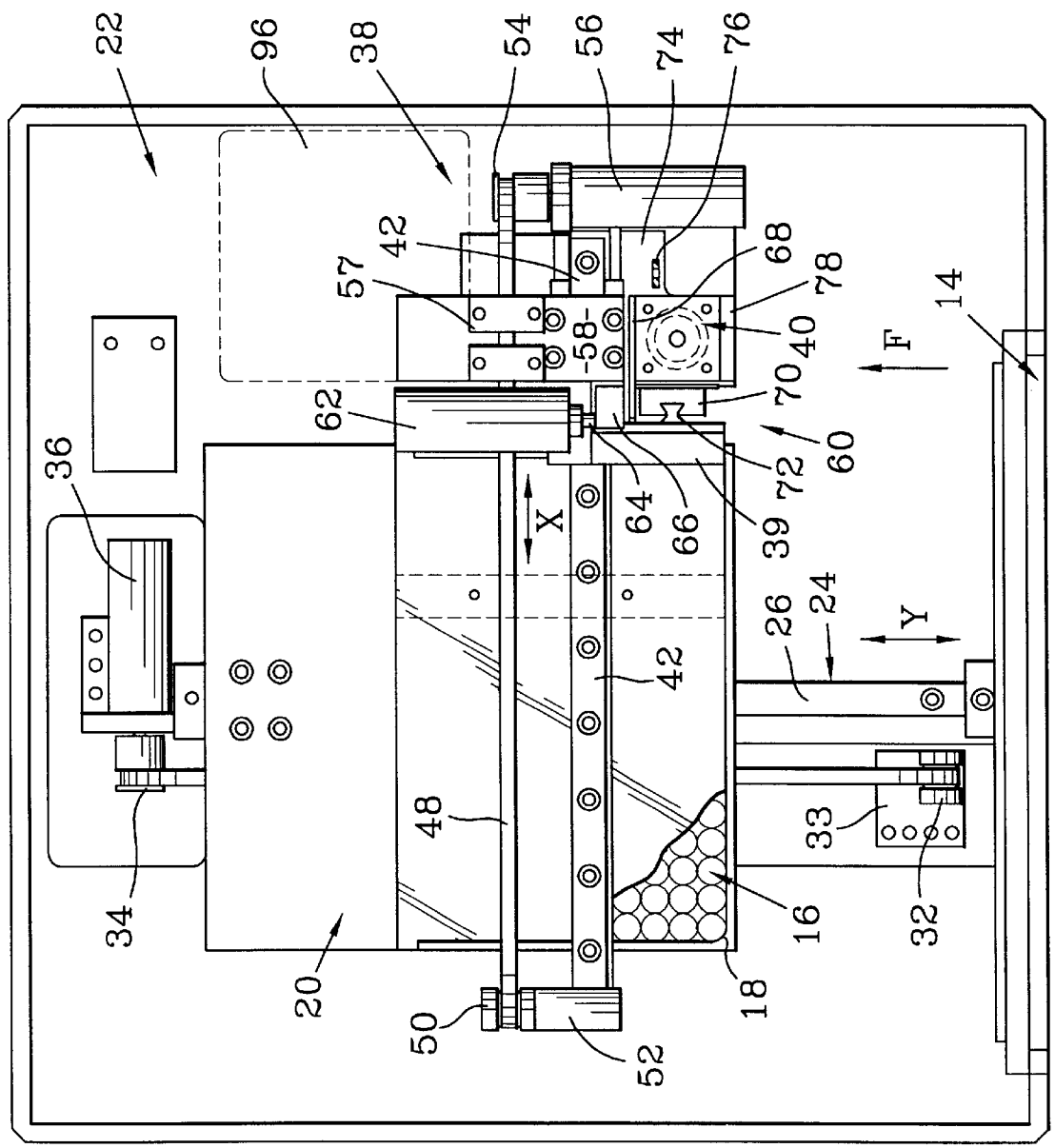
Figure 3:
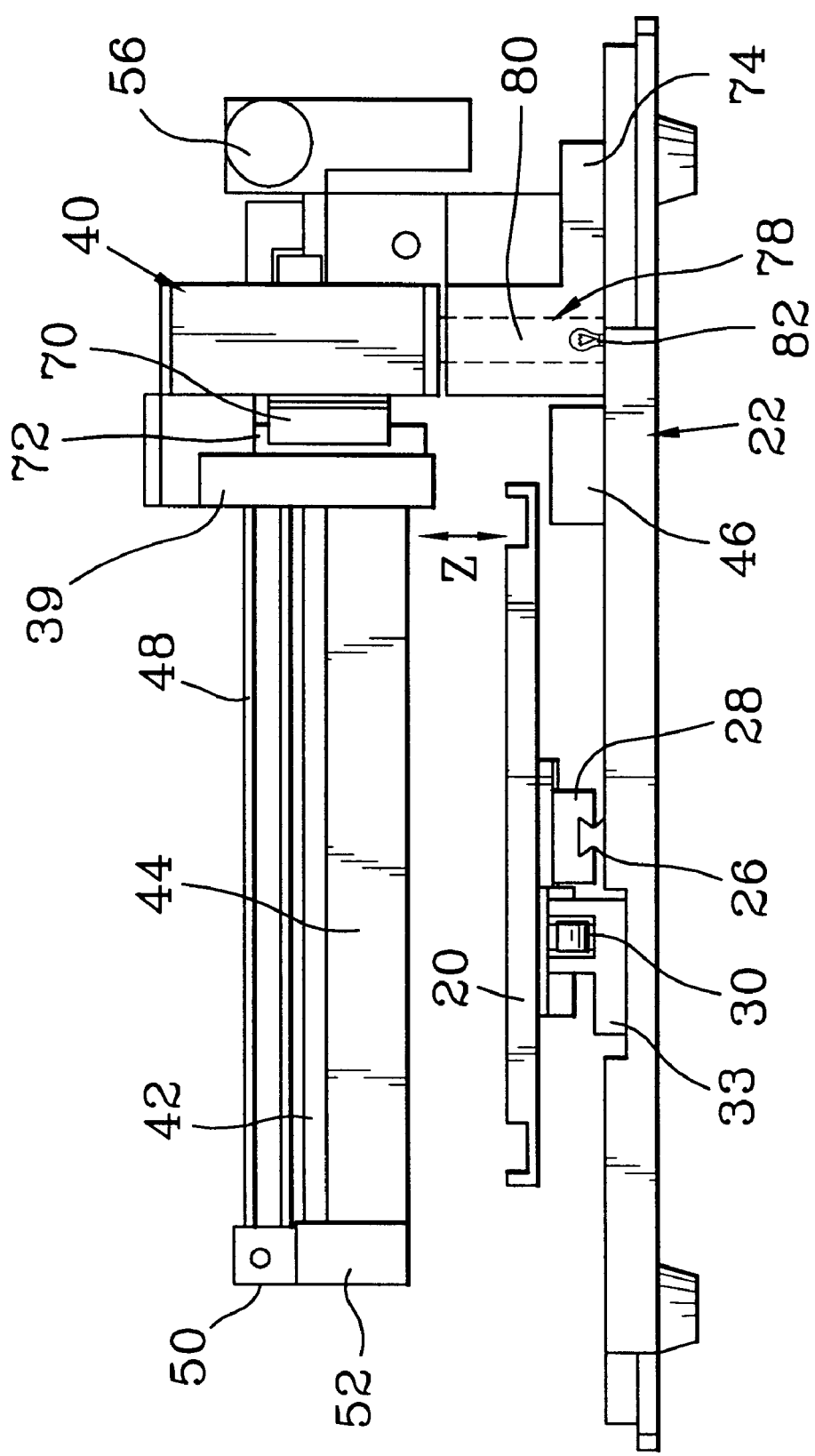
Figure 4A:
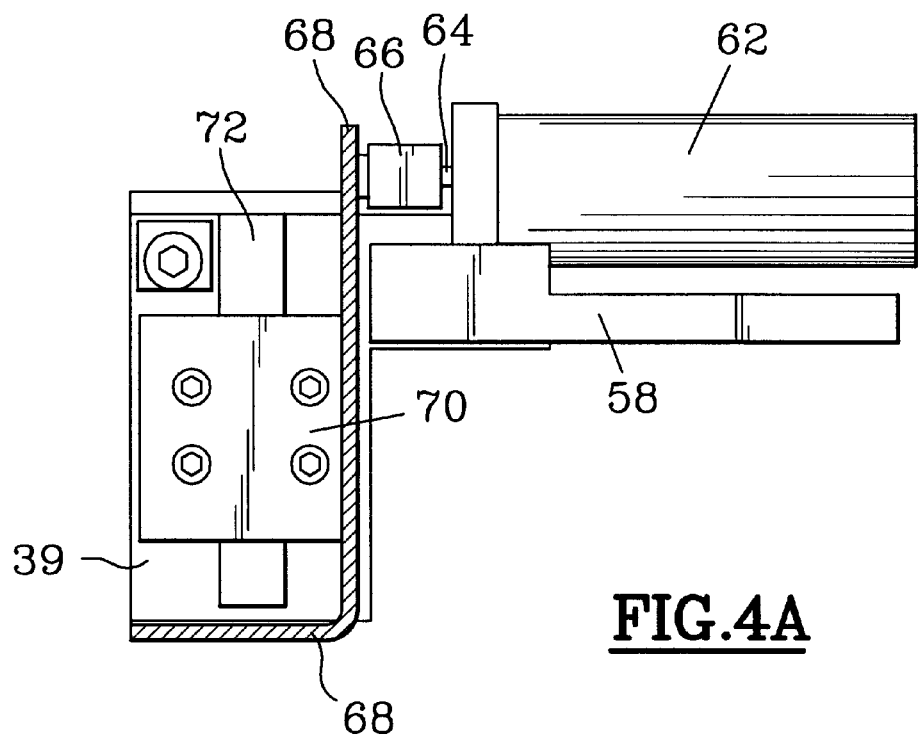
Figure 4B:
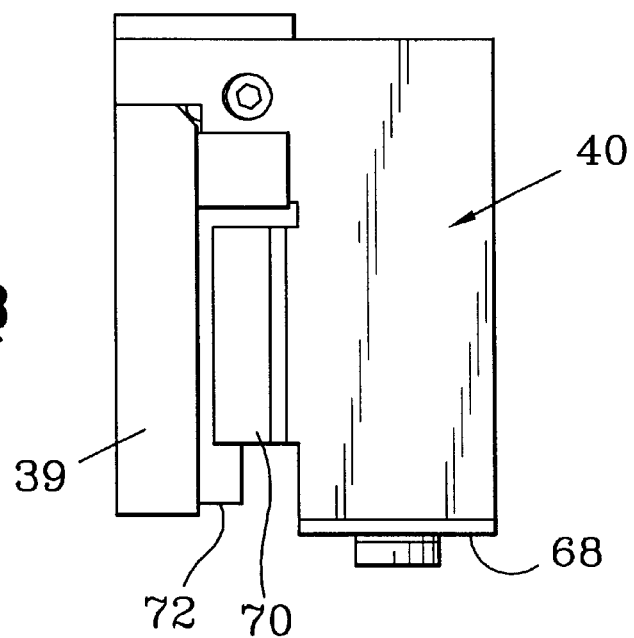

Referring now to FIGS. 2 and 3, on which the identical elements bear the same reference numerals, these figures show the interior of the luminometer of FIG. 1.

The luminometer comprises a chassis 22 comprising first means 24 for displacement in translation along the Y axis.

These first means 24 comprise, in the non-limiting example shown, a guide rail 26 on which is slidably mounted a carriage 28 (see FIG. 3), secured to the platform 20 supporting the microtitration plate 16.

An assembly of a belt 30 stretched between a roller 32 carried by a base 33 and the drive pulley 34 of a motor 36 with an integrated encoder, coacts with the carriage 28 so as to displace this latter on the rail 26 with a translatory movement in both directions, symbolized by an arrow, with perfectly controlled displacement.

There are also provided two means 38 for displacement in translation, along the axis x, provided to ensure the displacement of a frame 39 supporting a detector 40, symbolized by a double arrow in FIG. 2.

These displacement means 38 comprise a rail 42 fixed on a beam 44 of great rigidity, secured to the chassis 22 by a foot 46 and a belt assembly 48, extending between a roller 50 carried by a base 52 and the drive pulley 54 of a motor 56 with a integrated encoder.

A carriage 58 is secured to the belt 48 by grips 57 connected to said carriage so as to displace this latter along the rail 42 with a translatory movement in both directions along the X axis with perfectly controlled displacement.

The carriage 58 carries the frame 39 on which are connected the third translatory displacement means 60, along the Z axis.

These third translatory displacement means 60 comprise a motor 62 with an integrated encoder, whose output shaft 64 is fixed to a cam 66 which actuates a movable platform 68 on which is mounted the detector 40.

The platform 68 is secured to a carriage 70, slidably mounted on a rail 72 carried by the frame 39.

The displacements along the Z axis are of small amplitude.

The chassis is moreover provided with an abutment 74, having an end of path indicator 76, permitting zeroing.

At the level of this abutment, the apparatus is moreover provided with calibrating means 78 represented schematically in the figure as a well 80 and a lamp 82. The well is thus a simple open recess on which comes to rest the detector upon its return into neutral position, such that said detector will not be disturbed by the excess of light from the exterior, as described above. The lamp is on the contrary a source of constant light, sheltered from any outside disturbance, at the bottom of the well, which permits restarting the detector when necessary to compensate possible drift.

Figure 5:
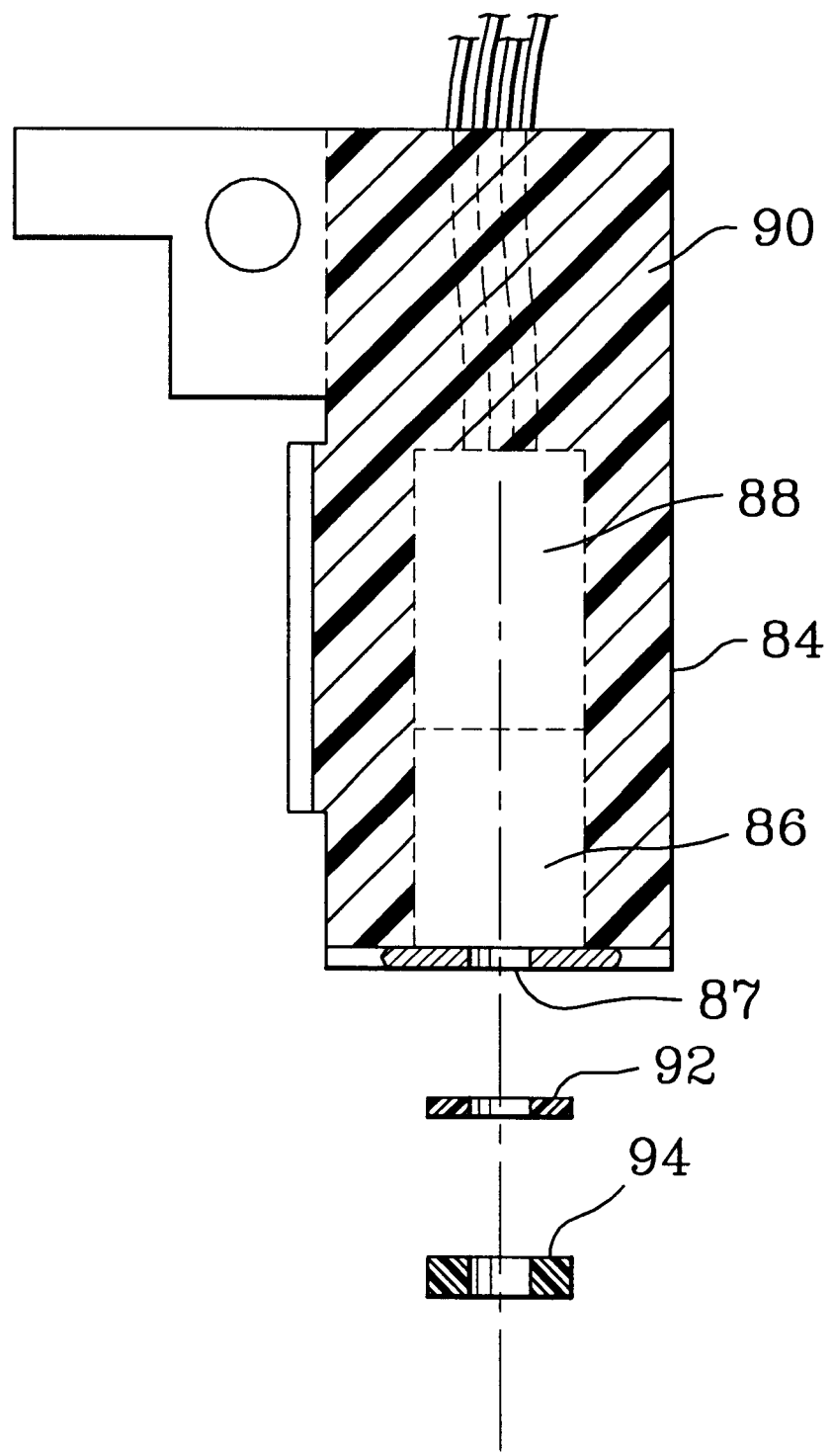

In FIG. 5, there is seen the detector 40 alone. This detector is schematically shown with a casing 84, an optical portion 86 of the photomultiplier type with a window 87, an electronic portion 88 for the acquisition of measurements and a large portion 90 of resin base ensuring effective shielding.

Such a detector is particularly sold by the HAMAMATSU company. This detector has a rapid response time, sufficient measurement sensitivity, is substantially insensitive to magnetic and electromagnetic disturbances, even of high power, and above all is insensitive to vibrations and to accelerations engendered by mechanical displacements.

In this same FIG. 5, there is also shown an adaptation for the envisaged use, namely, a superposition of a first ring 92, of flexible material such as foam, and a second ring 94 of polymeric material but of greater hardness, provided to come into contact with the microwells or the tubes, these rings being centered relative to the measuring window 87 of the detector.

This assembly permits compensating the errors of planarity of the microwells relative to the detector by creating a substantially perfect seal between the microwells and the detector so as to suppress the light contamination of the measurement from an external source. This simple mountain is altogether applicable for this small surface. It is also to be noted that the hardest material is adjacent the product to be assayed, which is a measure of cleanliness because it maintains its integrity after multiple contacts, which could not be guaranteed only with a ring of foam.

The luminometer is completed by an electronic assembly for processing data, with a memory, not shown, only the amplification module 96 of the signal being shown in broken line in FIG. 2, because this module, for reasons of gain in sensitivity, is mounted on and carried by the carriage 58. Thus, it is necessary to decrease as much as possible the connections by cables between the detector and this amplifier, the digitized output signal of this module being adapted itself to be carried without problem.

The operation is indicated hereafter with respect to the embodiment shown in the different figures, but it corresponds also generally to the operation of the luminometer once integrated into another device as indicated above.

The user who desires to carry out measurements of luminometry on biological media first prepares his microtitration plate with the microwells in which are disposed the products to be studied.

He then introduces the plate through opening 12 to dispose it on the movable platform 20, which projects to facilitate this positioning.

It is to be noted that the measurements of photons emitted by the reaction medium are possible during sufficiently long periods because the reactions are slow and especially what often matters is to raise the reaction rate more than a flash measurement.

The measurements are then taken in a preprogrammed order which does not directly involve the invention. By contrast, the movements from one microwell to another are always identical. The motors 36 and 56 are supplied and controlled by the encoders to position the detector in alignment with a given microwell. As soon as the detector is in alignment with this microwell, the motor 62 is supplied to lower the detector 40 along the Z axis. The amplitude of movement is known and the spacings are compensated by rings 92 and 94. The window 87 of the detector is centered on the microwell and all contamination of photons emitted by the adjacent microwells is removed.

The determination of the height of each well by the encoder associated with the motor 62 permits, if necessary, an individualized and tailored treatment for each well and the possible use of various plates of wells as well as a control of the presence of the wells.

Measurement is carried out and the results acquired are processed and transferred into the associated memory for a paper printout and/or an ultimate assay.

The detector having a low duration of remanance, it is almost immediately ready for a new measurement. The interval of time between two measurements is of the order of one second, by way of example.

The different measurements are thus conducted one after the other.

Once the assembly of the microwells has been visited, the detector is brought into alignment with the abutments 78 and lowered to bear against the storage well 80. A derivative control can be carried out by initiating the detector. It suffices to light the lamp and to carry out a measurement of the photons emitted whose quantity is completely known.

It can be noted that the use of the type of compact and specific detector as indicated above, leads to numerous advantages, particularly the compactness, the simplicity and hence the reliability, the high sensitivity because the detection of photons is carried out directly above the product well amplified immediately afterward, within the same detector, without need to conduct the photons to a photomultiplier that is more distance with losses and disturbances to which this can give rise.

Of course the movements of the movable support platform for the microtitration plaque can be carried out in the X and Y directions directly and leaving only the movement in the Z direction, but that gives rise to a larger device which is a little more complicated as to the positioning of the various elements, and this is why the arrangement described above is considered as the best embodiment.

Figure 6:
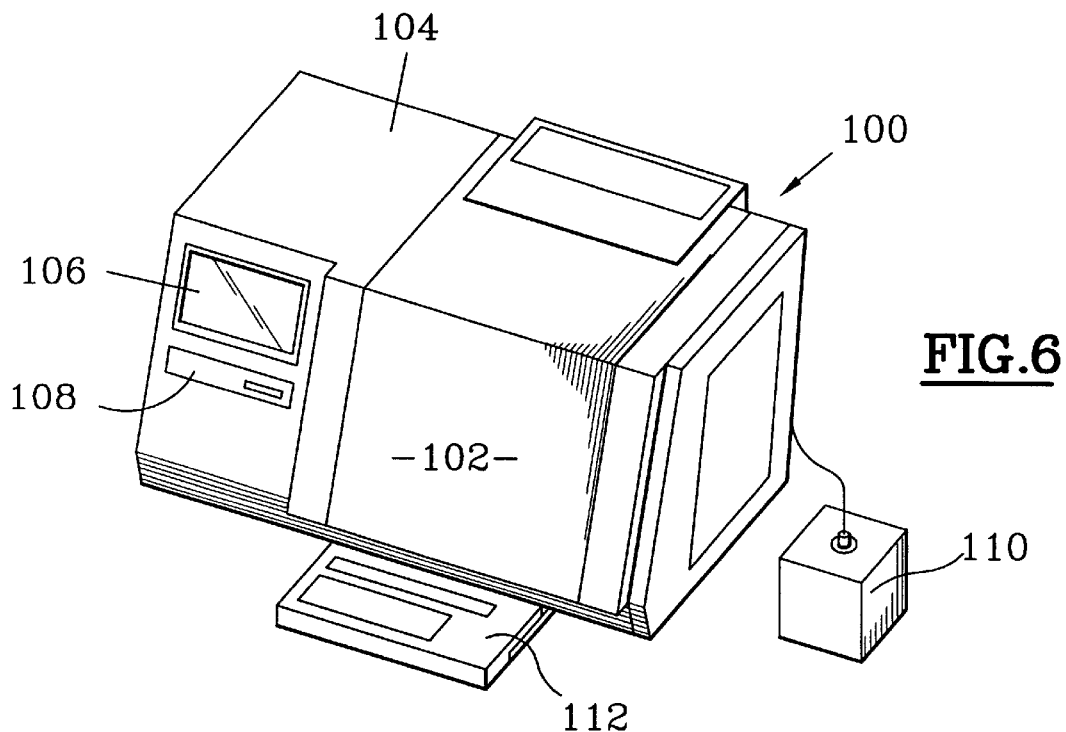
Figure 7:
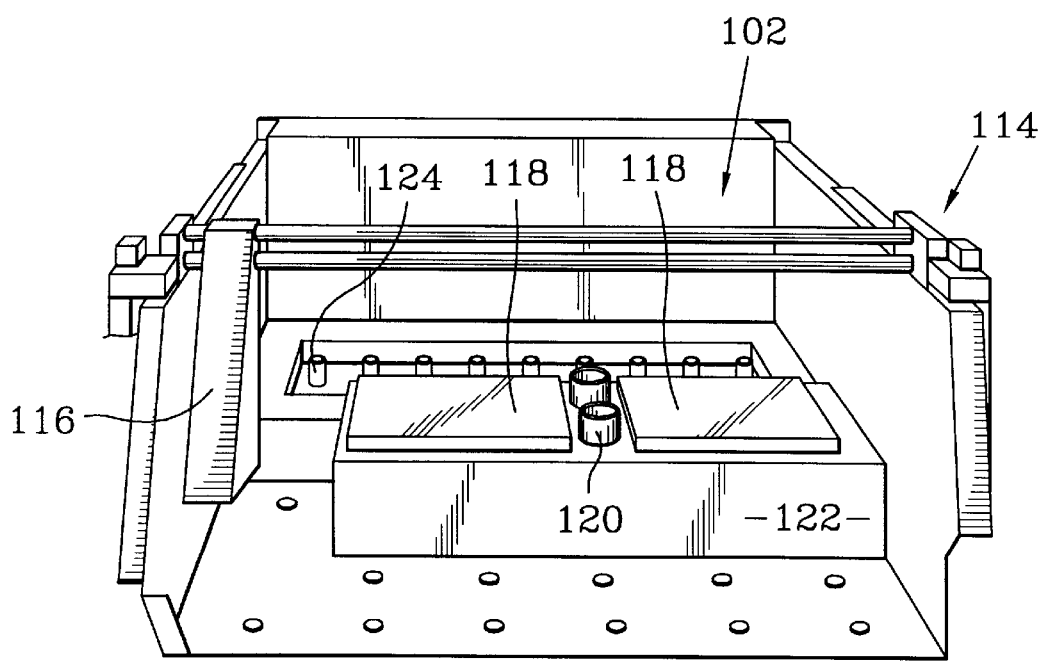

In FIG. 6, there is shown a measuring device described in European patent application EP-A-92/450 011, in which device is integrated the luminometer according to the invention, so as to augment its capabilities.

This device comprises a cover 100 protecting the measurement region 102 itself, an electronic module 104 integrated with a display screen 106 and a memory unit with a diskette reader 108, a discard receptacle 110 as well as a control keyboard 112.

The measurement region 102 comprises an X-Y table 114 permitting the displacement of a measuring head 116 carrying the different instruments for sampling and assay.

Substantially at the center of the measuring region, there are disposed supports 118 for microtitration plates as well as an injection orifice 120 for specimens of a spectrophotometer, not shown, and disposed in the base 122.

There is also schematically shown mechanical elements to position the reactive contents for example, by reference numeral 124.

Figure 8:
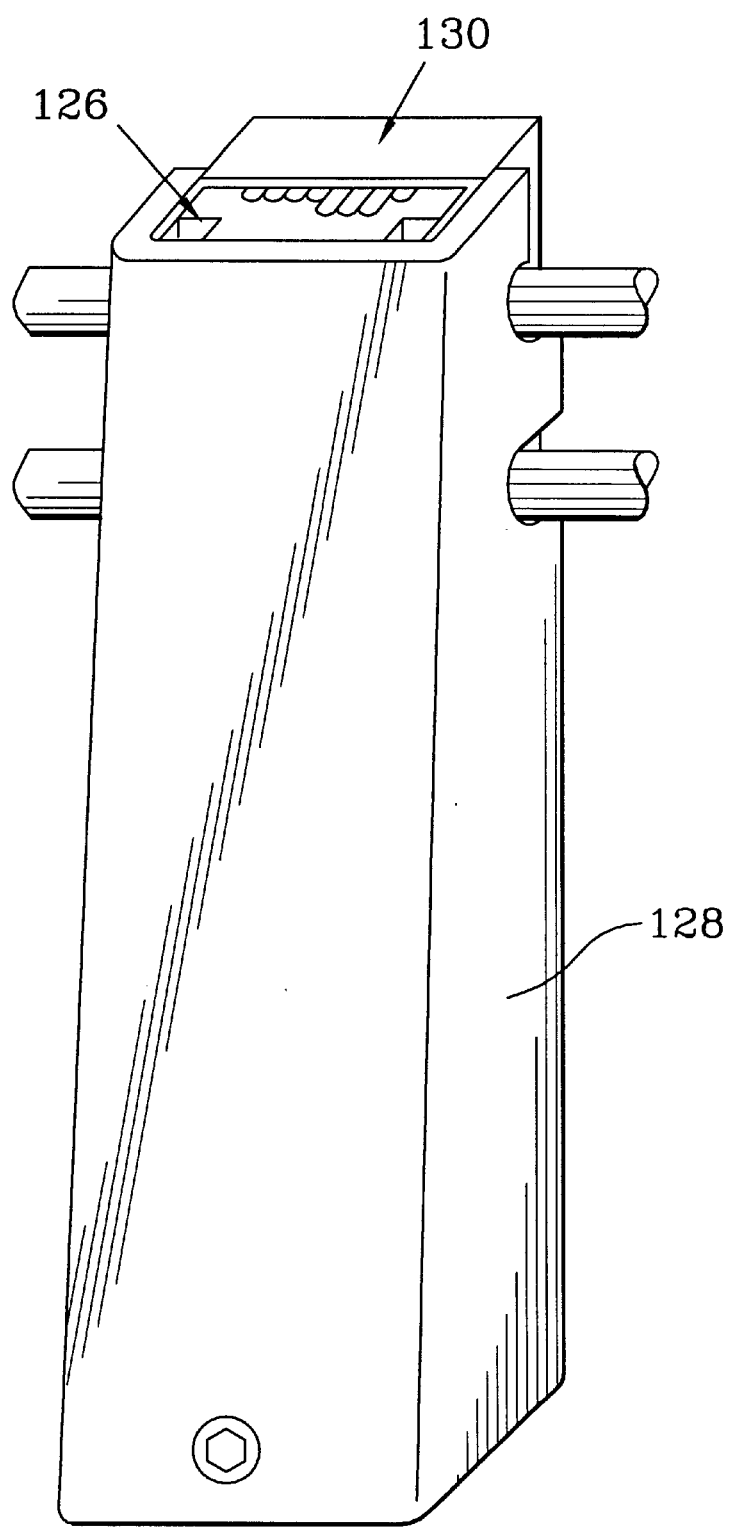

In FIG. 8, there is shown the head 116 itself, which comprises a front surface 126 with a transparent casing 128 and a rear surface 130 in which, according to the embodiment in question, there is disposed and integrated the luminometer according to the invention.

Figure 9:
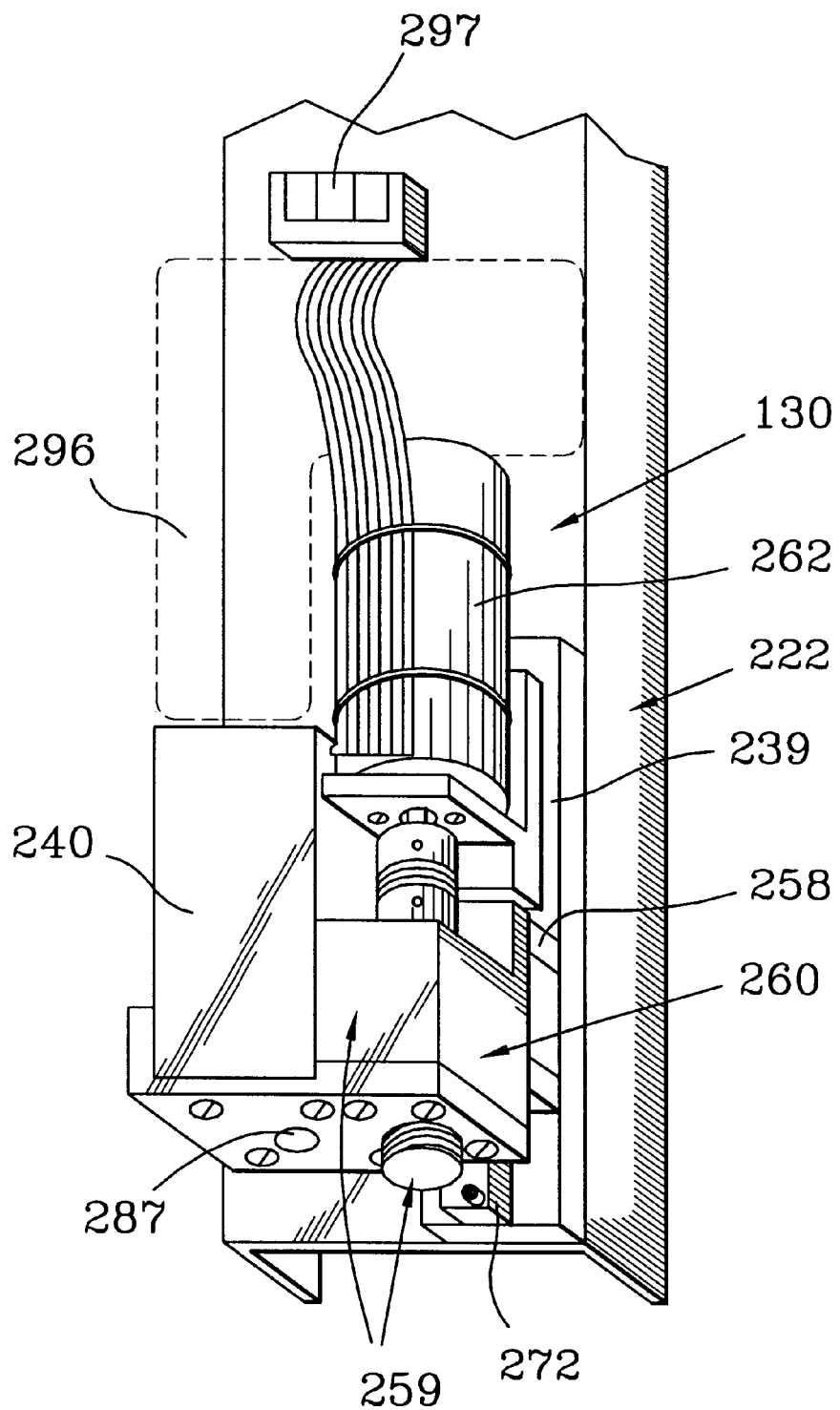

It is this rear surface 130 which is shown in detail in FIG. 9.

The X-Y movements are already carried out for the positioning of the head such that in FIG. 9, only the translational displacement means along the Z axis are shown.

For purposes of this description and by analogy with the first embodiment, the identical elements or elements which at least play the same role, are shown with the same reference numerals but adding 200.

The means 260 for translational displacement along the Z axis comprise a base 239 supporting a rail 272 oriented vertically and secured to the chassis 222 of the head.

A carriage 258 is mounted movably in translation on said rail and comprises moreover a screw-nut assembly 259, the screw being driven by a motor 262 secured to the chassis 222.

The carriage carries, as before, a detector 240.

The amplification module 396 of the signal is disposed immediately adjacent the detector, directly on the chassis 222 and the head and the assembly of connections is given reference numeral 297.

It should be noted the extreme compactness of the assembly because the transfer section of the head is of the order of 5 cm.

The type of detector used permits resisting accelerations of 2 g to which the head is subjected. These great accelerations are due to the fact that there is room in the measuring device of FIG. 6 to provide a large X-Y table so as to carry out displacements of a relatively large movement with very short time durations and it should be noted that in this case, the X-Y movements are combined, which leads to curvilinear displacements of the head.

The fact of arranging a luminometer on the movable head permits measuring directly the photons emitted by the reaction recesses whilst the spectrophotometer carries out measurements on the specimens, resulting in a reaction, injected in a suitable receptacle.

Also, the direct measurement is a particularly attractive advantage for biological assays, in particular hormonal tests. To give an order of magnitude of the scale of sensitivity, the spectrophotometer varies from 1 to 3,000 and the luminometer from 1 to 500,000.

It will be understood that the interest in moving the detector in the Z direction is that the microtitration plate is, by its very design, stationary and it is difficult or even impossible to envisage moving it in the Z direction.

Of course, the detector indicated for carrying out the preferred embodiment can be replaced by any other detector whose integration and design permits it to be free from vibrations whilst having a sufficient sensitivity of measurement with high resistance to external disturbances of magnetic or electromagnetic origin, thereby permitting its integration and its operation in an industrial medium.

Of course, for simplicity of description, it has been considered that the three axes X, Y and Z were oriented with a plane X, Y horizontal and the axis Z vertical, but the reference framework thus provided could be oriented as a function of need, without departing from the scope of the invention.

What is claimed is:

1. Luminometer comprising a chassis protected by a cover whose interior is accessible past a closure flap, a detector for measuring photons with a measuring window, a platform supporting specimen plates, an electronic module for amplification and digitizing data and an electronic module for processing these data, wherein the measuring detector is movable and said luminometer comprises motor means for displacing said detector at least along the Z axis, wherein the chassis is provided with means for displacement in translation only along one of the axes of the plane, the axis Y, and the detector and the means for displacement in translation along the Z axis are carried by a means for displacement in translation along the other of the axes of the plane, the axis X, and wherein the means for displacement in the Z direction comprises a carriage mounted slidably on a rail oriented along the axis Z and a motor with an integrated encoder secured t o a frame, driving a cam in rotation provide d to ensure said displacement in translation, this frame being carried by a carriage mounted slidably on a rail, supported by a beam mounted at one of its ends, oriented along the X axis, said carriage being driven by an assembly of a belt stretched between a roller and a pulley of a motor with an integrated encoder.

2. Luminometer according to claim 1, wherein the detector comprises an assembly of a photomultiplier and a second electronic module being integrated, the assembly being protected by shielding.

3. Luminometer according to claim 1, further comprising means for sealing and for compensation of errors of planarity in line with the measurement window.

4. Luminometer comprising a chassis protected by a cover whose interior is accessible past a closure flap, a detector for measuring photons with a measuring window, a platform supporting specimen plates, an electronic module for amplification and digitizing data and an electronic module for processing these data, wherein the measuring detector is movable and said luminometer comprises motor means for displacing said detector at least along the Z axis, wherein the chassis is provided with means for displacement in translation only along one of the axes of the plane, the axis Y, and the detector and the means for displacement in translation along the Z axis are carried by a means for displacement in translation along the other of the axes of the plane, the axis X, and further comprising an abutment at one of the ends of the movement in the X direction, provided with an end of path indicator permitting an initialization of the movements, a black well permitting parking the detector shielded from parasitic disturbances and a calibrating lamp disposed in said black well permitting calibrating the detector as needed.

5. Luminometer comprising a chassis protected by a cover whose interior is accessible past a closure flap, a detector for measuring photons with a measuring window, a platform supporting specimen plates, an electronic module for amplification and digitizing data and an electronic module for processing these data, wherein the measuring detector is movable and said luminometer comprises motor means for displacing said detector at least along the Z axis, wherein the chassis is provided with means for displacement in translation only along one of the axes of the plane, the axis Y, and the detector and the means for displacement in translation along the Z axis are carried by a means for displacement in translation along the other of the axes of the plane, the axis X, and wherein the electronic module for amplification and digitizing the data is carried by means for displacement in translation along the X axis and disposed immediately adjacent the detector.

6. Luminometer comprising a chassis protected by a cover whose interior is accessible past a closure flap, a detector for measuring photons with a measuring window, a platform supporting specimen plates, an electronic module for amplification and digitizing data and an electronic module for processing these data, wherein the measuring detector is movable and said luminometer comprises means for displacing said detector at least along the Z axis;

wherein the chassis is provided with means for displacement in translation only along one of the axes of the plane, the axis Y, and the detector and the means for displacement in translation along the Z axis are carried by a means for displacement in translation along the other of the axes of the plane, the axis X; and wherein the means for displacement in the Z direction comprises a carriage mounted slidably on a rail oriented along the axis Z and a motor with an integrated encoder secured to a frame, driving a cam in rotation provided to ensure said displacement in translation, this frame being carried by a carriage mounted slidably on a rail, supported by a beam mounted at one of its ends, oriented along the X axis, said carriage being driven by an assembly of a belt stretched between a roller and a pulley of a motor with an integrated encoder.

7. Luminometer according to claim 6, further comprising an abutment at one of the ends of the movement in the X direction, provided with an end of path indicator permitting an initialization of the movements, a black well permitting parking the detector shielded from parasitic disturbances and a calibrating lamp disposed in said black well permitting calibrating the detector as needed.

8. Luminometer according to claim 6, wherein the electronic module for amplification and digitizing the data is carried by means for displacement in translation along the X axis and disposed immediately adjacent the detector.

9. Luminometer according to claim 6, wherein the detector comprises an assembly of a photomultiplier and a second electronic module being integrated, the assembly being protected by shielding.

10. Luminometer according to claim 6, further comprising means for sealing and for compensation of errors of planarity in line with the measurement window.

11. Measuring device comprising at least one support for a microtitration plate, a movable head, provided with means for measuring different physico-chemical parameters, means for displacement in translation of said head along the X and Y axes, comprising a luminometer integrated into the head according to claim 6, provided with single means for displacement in translation along the Z axis.

12. Device according to claim 11, wherein the displacement along the Z axis is obtained by means for displacement in translation of the screw/nut type.

* * * * *